US012749586B2

(12) United States Patent
Sharp et al.

(10) Patent No.: US 12,749,586 B2
(45) Date of Patent: Sep. 29, 2026

(54) ELECTRONIC CREATION, CURATION, APPROVAL AND DELIVERY OF HEALTH-RELATED, EDUCATIONAL CONTENT

(71) Applicant: SHORELINE SOLUTION LLC, Salt Lake City, UT (US)

(72) Inventors: Charles Sharp, Salt Lake City, UT (US); Amber Sawaya, Salt Lake City, UT (US); Gary Laben, Dallas, TX (US); Dennis Kooker, McKinney, TX (US); Ken Snyder, South Jordan, UT (US)

(73) Assignee: SHORELINE SOLUTION LLC, Salt Lake City, UT (US)

( * ) Notice: Subject to any disclaimer, the term of this patent is extended or adjusted under 35 U.S.C. 154(b) by 0 days.

(21) Appl. No.: 18/926,186

(22) Filed: Oct. 24, 2024

(65) Prior Publication Data

US 2025/0132059 A1 Apr. 24, 2025

Related U.S. Application Data

(60) Provisional application No. 63/592,855, filed on Oct. 24, 2023.

(51) Int. Cl.

| | |
|---|---|
| ***G16H 70/20*** | (2018.01) |
| ***G06Q 50/20*** | (2012.01) |
| ***G16H 10/60*** | (2018.01) |

(52) U.S. Cl.

CPC ............ *G16H 70/20* (2018.01); *G06Q 50/20* (2013.01); *G16H 10/60* (2018.01)

(58) Field of Classification Search

CPC ........ G16H 70/20; G16H 10/60; G16H 40/67; G16H 80/00; G06Q 50/20

See application file for complete search history.

(56) References Cited

U.S. PATENT DOCUMENTS 10,984,128 B1 * 4/2021 Hoffer .................... G16B 50/30
12,008,139 B1 * 6/2024 Hassad .................. G16H 10/60

(Continued)

FOREIGN PATENT DOCUMENTS

WO WO-2018125893 A1 * 7/2018 ............. G09B 19/00

OTHER PUBLICATIONS

Ladhar S, Koshman SL, Yang F, Turgeon R. Evaluation of Online Written Medication Educational Resources for People Living With Heart Failure. CJC Open. Jul. 12, 2022;4(10):858-865. doi: 10.1016/j.cjco.2022.07.004. PMID: 36254325; PMCID: PMC9568683. (Year: 2022).*

(Continued)

*Primary Examiner* — Sun M Li

(74) *Attorney, Agent, or Firm* — Bryan J. Massey

(57) ABSTRACT

An apparatus includes a condition module configured to determine a condition associated with a patient user. The apparatus includes a content module configured to select a content item from a group of content items based at least in part on the condition. The apparatus includes a clinician approval module configured to receive, from a clinician user associated with the patient user, approval of the content item. The apparatus includes a webpage module configured to generate, based at least in part on receiving the approval, a webpage comprising the content item. The apparatus includes a URL module configured to transmit a uniform resource locator ("URL") of the webpage to the patient user.

20 Claims, 8 Drawing Sheets

(56) References Cited

U.S. PATENT DOCUMENTS

| | | | | |
|---|---|---|---|---|
| 2012/0010904 A1* | 1/2012 | Buck | G16H 80/00 | |
| | | | 705/3 | |
| 2014/0099616 A1* | 4/2014 | Hussam | G09B 5/02 | |
| | | | 434/262 | |
| 2015/0046174 A1* | 2/2015 | Mainwaring | G16H 70/00 | |
| | | | 705/2 | |
| 2015/0379232 A1* | 12/2015 | Mainwaring | G16H 50/70 | |
| | | | 705/2 | |
| 2024/0143129 A1* | 5/2024 | Meriaz | G06F 3/0485 | |
| 2024/0177859 A1* | 5/2024 | Szamocki | G06F 40/40 | |

OTHER PUBLICATIONS

Thaker K, Chi Y, Birkhoff S, He D, Donovan H, Rosenblum L, Brusilovsky P, Hui V, Lee YJ. Exploring Resource-Sharing Behaviors for Finding Relevant Health Resources: Analysis of an Online Ovarian Cancer Community. JMIR Cancer. Apr. 12, 2022;8(2):e33110. doi: 10.2196/33110. PMID: 35258465; PMCID: PMC904414 (Year: 2022).*

Y. Zhou and D. Evans, "Understanding and Monitoring Embedded Web Scripts," 2015 IEEE Symposium on Security and Privacy, San Jose, CA, USA, 2015, pp. 850-865, doi: 10.1109/SP.2015.57. (Year: 2015).*

T. Bujlow, V. Carela-Español, J. Solé-Pareta and P. Barlet-Ros, "A Survey on Web Tracking: Mechanisms, Implications, and Defenses," in Proceedings of the IEEE, vol. 105, No. 8, pp. 1476-1510, Aug. 2017, doi: 10.1109/JPROC.2016.2637878. (Year: 2017).*

* cited by examiner

ELECTRONIC CREATION, CURATION, APPROVAL AND DELIVERY OF HEALTH-RELATED, EDUCATIONAL CONTENT

CROSS-REFERENCE TO RELATED APPLICATION

This application claims the benefit of U.S. Provisional Patent Application No. 63/592,855, filed Oct. 24, 2023, which is incorporated herein by reference.

FIELD

The subject matter disclosed herein relates to educational content, and more particularly relates to electronic creation, curation, approval, and delivery of health-related educational content.

BACKGROUND

Educational content can help patients and their friends and family understand more about a particular condition or course of treatment that they are experiencing.

SUMMARY

The subject matter of the present disclosure application has been developed in response to the present state of the art, and in particular, in response to the shortcomings of energy storage systems that have not yet been fully solved by currently available techniques. Accordingly, the subject matter of the present application has been developed to provide electronic creation, curation, approval, and delivery of health-related, educational content that overcomes at least some shortcomings of prior art techniques.

The following is a non-exhaustive list of examples, which may or may not be claimed, of the subject matter, disclosed herein.

Disclosed herein is an apparatus. The apparatus includes a condition module configured to determine a condition associated with a patient user, a content module configured to select a content item from a group of content items based at least in part on the condition, a clinician approval module configured to receive, from a clinician user associated with the patient user, approval of the content item, a webpage module configured to generate, based at least in part on receiving the approval, a webpage comprising the content item, and a URL module configured to transmit a uniform resource locator ("URL") of the webpage to the patient user. At least a portion of said modules include one or more of hardware circuits, programmable hardware circuits and executable code, the executable code stored on one or more computer readable storage media. The preceding subject matter of this paragraph characterizes example 1 of the present disclosure.

The URL module is further configured to transmit the URL via at least one of the following: an e-mail message, a text message, a wireless connection between the apparatus and a device associated with the patient user, or any combination thereof. The preceding subject matter of this paragraph characterizes example 2 of the present disclosure, wherein example 2 also includes the subject matter according to example 1, above.

The URL module is further configured to transmit the URL by transmitting a link to the URL to the patient user. The link is configured to navigate a device to the webpage without tracking an IP address of the device. The preceding subject matter of this paragraph characterizes example 3 of the present disclosure, wherein example 3 also includes the subject matter according to any of examples 1-2, above.

The content module is further configured to select the content item from the group of content items by selecting a plurality of content items from the group of content items based at least in part on the condition. The preceding subject matter of this paragraph characterizes example 4 of the present disclosure, wherein example 4 also includes the subject matter according to any of examples 1-3, above.

The webpage module is further configured to generate the webpage by embedding the content item in the webpage and the content item includes at least one of the following: video content, audio content, an image, a graphic, an additional link, and/or any combination thereof. The preceding subject matter of this paragraph characterizes example 5 of the present disclosure, wherein example 5 also includes the subject matter according to any of examples 1-4, above.

The content item includes educational material relating to the condition and the condition comprises at least one of: a characteristic of a patient's mental health, a characteristic of a patient's physical health, a diagnosis, or any combination thereof. The preceding subject matter of this paragraph characterizes example 6 of the present disclosure, wherein example 6 also includes the subject matter according to any of examples 1-5, above.

The webpage includes a private webpage of a user interface of an application. Electronic health records related to the patient user are accessible to the patient user via the application. The application includes at least one of a web application or a mobile application. The preceding subject matter of this paragraph characterizes example 7 of the present disclosure, wherein example 7 also includes the subject matter according to any of examples 1-6, above.

The content module is further configured to select the content item from the group of content items further based at least in part on at least one of: an association between the clinician user and the patient user, input from the clinician user, a patient demographic, or any combination thereof. The preceding subject matter of this paragraph characterizes example 8 of the present disclosure, wherein example 8 also includes the subject matter according to any of examples 1-7, above.

Further disclosed herein is a method. The method includes determining a condition associated with a patient user. The method also includes selecting a content item from a group of content items based at least in part on the condition. The method further includes receiving approval of the content item from a clinician user. The clinician user is associated with the patient user. The method additionally includes generating, based at least in part on receiving the approval, a webpage comprising the content item. The method also includes transmitting a uniform resource locator ("URL") of the webpage to the patient user. The preceding subject matter of this paragraph characterizes example 9 of the present disclosure.

Transmitting the URL includes transmitting a link to the webpage to the patient user. The link is configured to navigate a device to the webpage without tracking an IP address of the device. The preceding subject matter of this paragraph characterizes example 10 of the present disclosure, wherein example 10 also includes the subject matter according to example 9, above.

The method further includes receiving a content item to be added to the group of content items. The method also includes transmitting, to an approval user, a request for approval of the content item. The method additionally includes presenting, to the approval user via graphical user interface (GUI), the content item and a button that is selectable to add the content item to the group of content items. The method further includes, in response to input from the approval user selecting the button, adding the content item to the group of content items. Adding the content item to the group of content items comprises displaying the content item to the clinician user and additional clinician users via an additional GUI. The preceding subject matter of this paragraph characterizes example 11 of the present disclosure, wherein example 11 also includes the subject matter according to any of examples 9-10, above.

The method further includes receiving text input from the approval user and embedding the text input into the content item. The preceding subject matter of this paragraph characterizes example 12 of the present disclosure, wherein example 12 also includes the subject matter according to example 11, above.

The condition includes a health condition and the content item comprises at least one of video, audio, text, or image. The preceding subject matter of this paragraph characterizes example 13 of the present disclosure, wherein example 13 also includes the subject matter according to any of examples 9-12, above.

The method further includes determining a health condition related to the content item based at least in part on at least one of input from a user or machine learning analysis of the content item and tagging the content item based at least in part on the health condition related to the content item. The preceding subject matter of this paragraph characterizes example 14 of the present disclosure, wherein example 14 also includes the subject matter according to any of examples 9-13, above.

The method further includes transmitting a link to the URL to the patient user and to one or more additional users associated with the patient. The preceding subject matter of this paragraph characterizes example 15 of the present disclosure, wherein example 15 also includes the subject matter according to any of examples 9-14, above.

The content is downloadable from the webpage. The preceding subject matter of this paragraph characterizes example 16 of the present disclosure, wherein example 16 also includes the subject matter according to any of examples 9-15, above.

The method further includes storing one or more promotional content items, selecting, based at least in part on the condition associated with the patient, a promotional content item of the promotional content items, and uploading the promotional content item to the webpage. The preceding subject matter of this paragraph characterizes example 17 of the present disclosure, wherein example 17 also includes the subject matter according to any of examples 9-16, above.

The method further includes determining a first time and/or date to share the content item with the patient. Generating the webpage and transmitting the URL is performed at the determined date and/or time. The preceding subject matter of this paragraph characterizes example 18 of the present disclosure, wherein example 18 also includes the subject matter according to any of examples 9-17, above.

The content item comprises a first content item. The method further includes determining, for a second content item, a second time and/or date to share the content item with the patient. The second time and/or date is different from the first time and/or date. The method also includes on or after the second time and/or date, performing at least one of the following actions. The method additionally includes uploading the second content item to the webpage. The method further includes generating an additional webpage displaying the second content item. Transmitting at least one of the URL or an additional URL of the additional webpage to the patient. The preceding subject matter of this paragraph characterizes example 19 of the present disclosure, wherein example 19 also includes the subject matter according to example 18, above.

Additionally disclosed herein is a program product including a non-transitory, computer readable storage medium that stores code executable by a processor. The executable code includes code to perform determining a condition associated with a patient user, selecting a content item from a group of content items based at least in part on the condition, and receiving, from a clinician user associated with the patient user, approval of the content item. The code is further executable to perform, based at least in part on receiving the approval, generating a webpage comprising at least one of the content item, and transmitting a uniform resource locator ("URL") of the webpage to the patient user. The preceding subject matter of this paragraph characterizes example 20 of the present disclosure.

BRIEF DESCRIPTION OF THE DRAWINGS

A more particular description of examples of the present disclosure will be rendered by reference to specific examples that are illustrated in the appended drawings. Understanding that these drawings depict only some examples and are not therefore to be considered to be limiting of scope, the examples will be described and explained with additional specificity and detail through the use of the accompanying drawings, in which.

DETAILED DESCRIPTION

Figure 1:
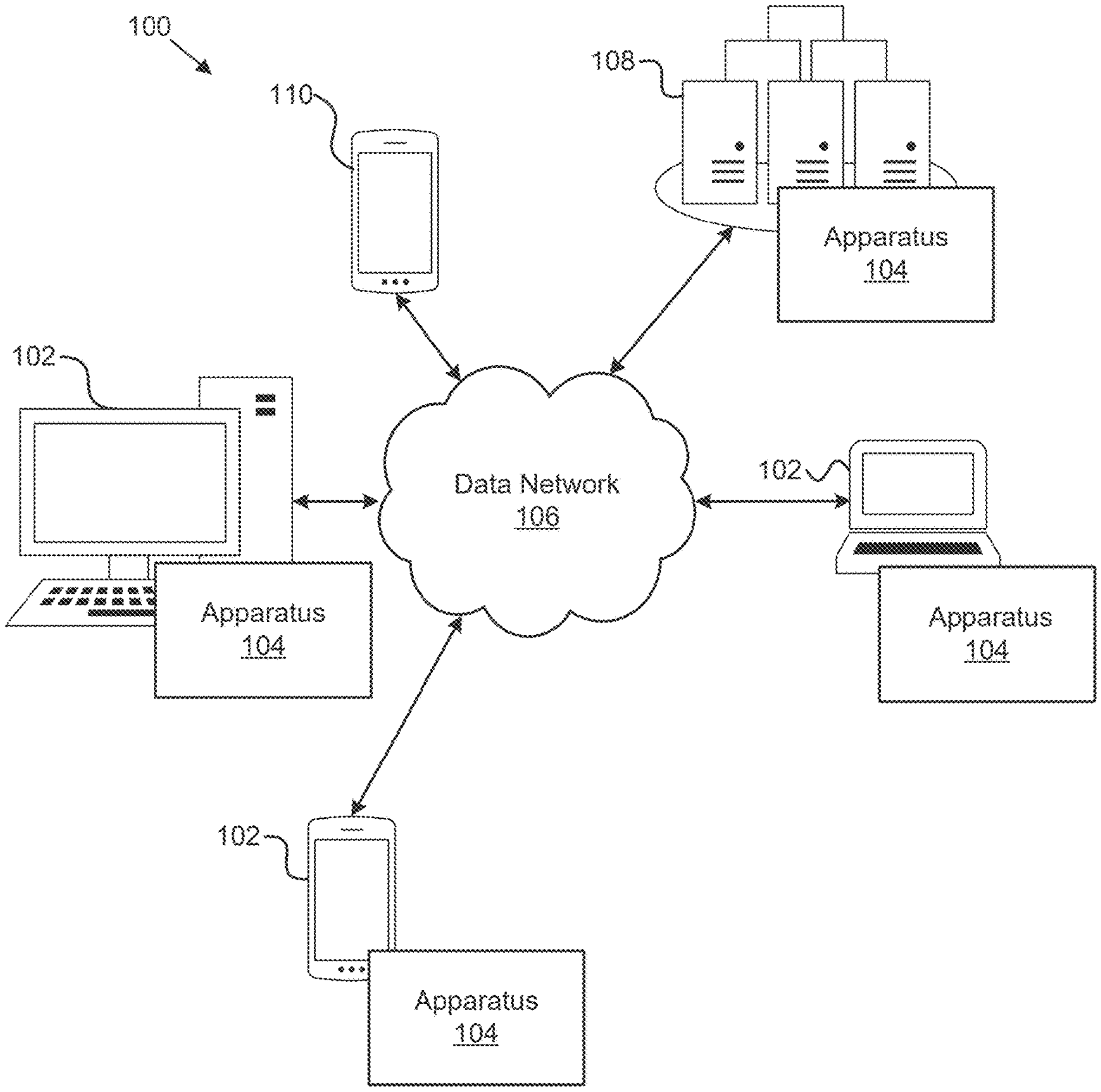
FIG. 1 is a schematic block diagram illustrating one example of a system for electronic creation, curation, approval, and delivery of health-related, educational content.

As will be appreciated by one skilled in the art, aspects of the examples may be embodied as a system, method or program product. Accordingly, examples may take the form of an entirely hardware example, an entirely software example (including firmware, resident software, micro-code, etc.) or an example combining software and hardware aspects that may all generally be referred to herein as a "circuit," "module" or "system." Furthermore, examples may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain example, the storage devices only employ signals for accessing code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for examples may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one example," "an example," or similar language means that a particular feature, structure, or characteristic described in connection with the example is included in at least one example. Thus, appearances of the phrases "in one example," "in an example," and similar language throughout this specification may, but do not necessarily, all refer to the same example, but mean "one or more but not all examples" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the examples may be combined in any suitable manner. In the following description, numerous specific details are provided, such as examples of programming, software modules, user selections, network transactions, database queries, database structures, hardware modules, hardware circuits, hardware chips, etc., to provide a thorough understanding of examples. One skilled in the relevant art will recognize, however, that examples may be practiced without one or more of the specific details, or with other methods, components, materials, and so forth. In other instances, well-known structures, materials, or operations are not shown or described in detail to avoid obscuring aspects of an example.

Aspects of the examples are described below with reference to schematic flowchart diagrams and/or schematic block diagrams of methods, apparatuses, systems, and program products according to examples. It will be understood that each block of the schematic flowchart diagrams and/or schematic block diagrams, and combinations of blocks in the schematic flowchart diagrams and/or schematic block diagrams, can be implemented by code. These code may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various examples. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding examples. Indeed, some arrows or other connectors may be used to indicate only the logical flow of the depicted example. For instance, an arrow may indicate a waiting or monitoring period of unspecified duration between enumerated steps of the depicted example. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate examples of like elements.

Clinicians often share important information with patients about their health conditions and/or treatment plans that can be difficult for the patient to remember if only shared once verbally. Often, when a patient receives a difficult health diagnosis and is unable to remember certain details about the diagnosis, the patient and/or friends and family of the patient look to resources on the Internet for answers to questions. However, Internet resources can be difficult to find, convoluted, and inaccurate, and may not pertain to the particular diagnosis of the patient.

According to examples of the present disclosure, electronic educational content can be given to the patient to help them remember important information regarding their diagnosis. Electronic educational content includes, for example, videos, short video clips, audio recordings, webpage posts, text documents, images, and/or graphics relating to a health condition and/or a course of treatment for that health condition. Educators, such as doctors, nurses, and patient educators, can create educational content to be shared with patients. For example, the educational content can be distributed to individuals and/or posted to a public webpage. However, creating and/or finding quality educational content on the relevant conditions for each patient can be time-consuming, particularly if the clinician is limited to sending the patient pre-approved content. Examples of the present disclosure help to provide patients with educational content tailored to their specific diagnosis, condition, and/or treatment plan. In some examples, the content is created or curated by the clinician themselves. Examples of the present disclosure also help to facilitate educational content creation, approval, curation, and/or delivery.

FIG. 1 is a schematic block diagram illustrating one example of a system 100 for electronic approval and delivery of health-related, educational content. As shown in FIG. 1, the system 100 includes at least one content apparatus 104 and a data network 106. The at least one content apparatus 104 is connected to the data network 106. The content apparatus 104 includes an apparatus configured to perform at least one of the following functions: creation of content, curation of content, approval of content, and/or transmission of content. Although not shown in FIG. 1, in some examples, the system 100 also includes a patient user device connected to at least one content apparatus 104 via the data network 106. The patient user device, for example, includes an information handling device configured to view and/or share content received from a content apparatus 104.

The content apparatus 104, in some examples, includes a semiconductor integrated circuit device (e.g., one or more chips, die, or other discrete logic hardware), or the like, such as a field-programmable gate array ("FPGA") or other programmable logic, firmware for an FPGA or other programmable logic, microcode for execution on a microcontroller, an application-specific integrated circuit ("ASIC"), a processor, a processor core, or the like. In one example, the content apparatus 104 may be mounted on a printed circuit board with one or more electrical lines or connections (e.g., to volatile memory, a non-volatile storage medium, a network interface, a peripheral device, a graphical/display interface, or the like). The hardware appliance may include one or more pins, pads, or other electrical connections configured to send and receive data (e.g., in communication with one or more electrical lines of a printed circuit board or the like), and one or more hardware circuits and/or other electrical circuits configured to perform various functions of the content apparatus 104.

The semiconductor integrated circuit device or other hardware appliance of the content apparatus 104, in certain examples, includes and/or is communicatively coupled to one or more volatile memory media, which may include but is not limited to random access memory ("RAM"), dynamic RAM ("DRAM"), cache, or the like. In one example, the semiconductor integrated circuit device or other hardware appliance of the content apparatus 104 includes and/or is communicatively coupled to one or more non-volatile memory media, which may include but is not limited to: NAND flash memory, NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon ("SONOS"), resistive RAM ("RRAM"), programmable metallization cell ("PMC"), conductive-bridging RAM ("CBRAM"), magneto-resistive RAM ("MRAM"), dynamic RAM ("DRAM"), phase change RAM ("PRAM" or "PCM"), magnetic storage media (e.g., hard disk, tape), optical storage media, or the like.

The data network 106, in one example, includes a digital communication network that transmits digital communications. The data network 106 may include a wireless network, such as a wireless cellular network, a local wireless network, such as a Wi-Fi network, a Bluetooth® network, a near-field communication ("NFC") network, an ad hoc network, and/or the like. The data network 106 may include a wide area network ("WAN"), a storage area network ("SAN"), a local area network ("LAN"), an optical fiber network, the internet, or other digital communication network. The data network 106 may include two or more networks. The data network 106 may include one or more servers, routers, switches, and/or other networking equipment. The data network 106 may also include one or more computer readable storage media, such as a hard disk drive, an optical drive, non-volatile memory, RAM, or the like.

The wireless connection may be a mobile telephone network. The wireless connection may also employ a Wi-Fi network based on any one of the Institute of Electrical and Electronics Engineers ("IEEE") 802.11 standards. Alternatively, the wireless connection may be a Bluetooth® connection. In addition, the wireless connection may employ a Radio Frequency Identification ("RFID") communication including RFID standards established by the International Organization for Standardization ("ISO"), the International Electrotechnical Commission ("IEC"), the American Society for Testing and Materials® (ASTM®), the DASH7™ Alliance, and EPCGlobal™.

Alternatively, the wireless connection may employ a ZigBee® connection based on the IEEE 802 standard. In one example, the wireless connection employs a Z-Wave® connection as designed by Sigma Designs®. Alternatively, the wireless connection may employ an ANT® and/or ANT+® connection as defined by Dynastream® Innovations Inc. of Cochrane, Canada.

The wireless connection may be an infrared connection including connections conforming at least to the Infrared Physical Layer Specification ("IrPHY") as defined by the Infrared Data Association® ("IrDA"®). Alternatively, the wireless connection may be a cellular telephone network communication. All standards and/or connection types include the latest version and revision of the standard and/or connection type as of the filing date of this application.

The one or more servers 108, in one example, may be embodied as blade servers, mainframe servers, tower servers, rack servers, and/or the like. The one or more servers 108 may be configured as mail servers, web servers, application servers, FTP servers, media servers, data servers, web servers, file servers, virtual servers, and/or the like. The one or more servers 108 may be communicatively coupled (e.g., networked) over a data network 106 to one or more information handling devices 102. For instance, a server 108 may be an intermediary between information handling devices 102 to facilitate sending and receiving electronic messages between the information handling devices 102.

In some examples, an information handling device 102 on which the apparatus 104 is deployed is in communication with an additional information handling device 110 over a connection to the data network 106. In some examples, the additional information handling device 110 is associated with a patient user, and the apparatus 104 is configured to present a user interface to be accessed by the patient user via the additional information handling device 110.

Figure 2:
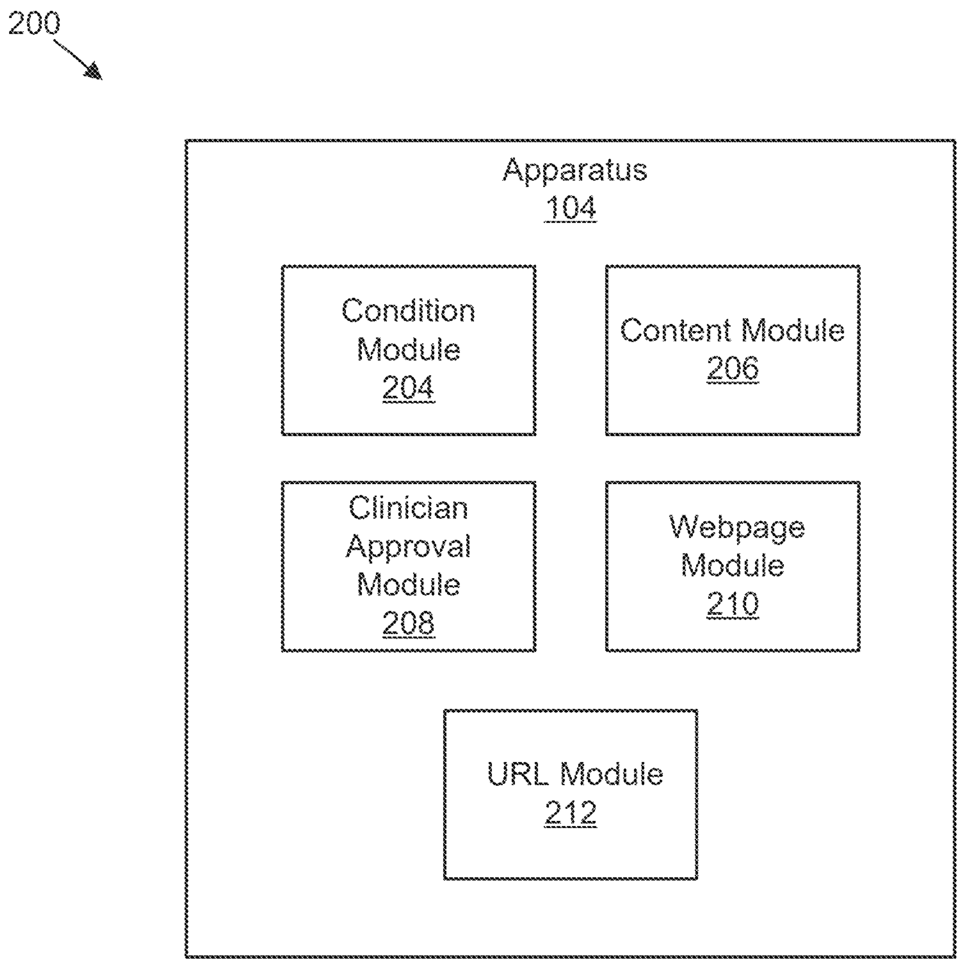
FIG. 2 is a schematic block diagram illustrating one example of an apparatus for electronic creation, curation, approval, and delivery of health-related, educational content.

FIG. 2 is a schematic block diagram illustrating one example of an apparatus 200 for electronic approval and delivery of health-related, educational content. In some examples, the apparatus 200 includes the content apparatus 104. The content apparatus 104, in some examples, includes one or more of a condition module 204, a content module 206, a clinician approval module 208, a webpage module 210, and a URL module 212, which are described in more detail below.

As used herein, the term "clinician" refers to any person communicating with a patient regarding a patient's health condition. A clinician includes, but is not limited to, a physician, nurse, physician's assistant, radiologist, surgeon, dentist, behavioral therapist, physical therapist, midwife, naturopath, medical student, and/or any combination thereof. As used herein, the term "patient" refers to any person receiving information from the clinician about a health condition, either on behalf of themselves or someone else. In some examples, a "patient" includes a person conversing with a clinician about their own health condition. In another example, a patient receives information from the clinician about a health condition of another. In such examples, the "patient" includes, for example, a family member (e.g., parent, child, grandparent, spouse, partner, next of kin, etc.), guardian, health care proxy, health care agent, medical power of attorney, and/or any combination thereof.

The condition module 204 is configured to determine a condition associated with the patient. As used herein, "condition" includes, for example, a characteristic of a patient's mental and/or physical health. A condition includes, for example, a diagnosis, illness (acute or chronic), disease, hereditary attribute, disability, injury, disorder, surgical complication, tumor, cyst, dermatological condition, orthodontic condition, cavity, gum disease and/or recession, blood sugar level, cholesterol level, vitamin or mineral level, vitamin or mineral deficiency, nutritional deficiency, lab result, scan result, MRI result, ultrasound result, test result, pregnancy, pregnancy complication, fertility issue, puberty, mental illness, and/or any combination thereof.

In some examples, the condition module 204 is configured to determine a condition for the patient based at least in part on at least one of: input from the patient's clinician, input from the patient, an electronic health record for the patient, content previously curated for the patient, and/or a combination thereof. In some examples, the condition module 204 determines the condition without recording and/or analyzing patient-clinician communication.

In some examples, the condition module 204 is configured to determine a treatment based at least in part on the determined condition. For example, the condition module 204 determines a condition of a specific type of cancer and determines that the patient may want to view content relating to chemotherapy.

The content module 206 is configured to select content items from a group of content items to send to the patient. In some examples, the content module 206 makes the selection based on at least one of: the condition determined by the condition module 204, input from the clinician, a patient demographic, or any combination thereof. In some examples, the content module 206 is configured to automatically select the content item in response to the condition module 204 determining the condition. In some examples, the content module 206 is configured to select the content item based on direct input from the clinician user (e.g., a selection received from the clinician user via a user interface).

A "content item" includes, for example, electronic educational content regarding a patient's condition and/or an upcoming treatment for that patient. In some examples, a content item includes data files with file types such as, but not limited to: video, audio, text, PDF, images, and/or any combination thereof. In some examples, the content items include at least one of the following: an image, a PDF pamphlet, a booklet, a link to another webpage, a video, an image, an infographic, an interactive graphic, a podcast episode, an article, and/or any combination thereof. For example, a content item can include a video of a doctor explaining an upcoming procedure. In another example, a content item includes a description of an exercise to be performed by the patient as part of a physical therapy routine. Yet another example of a content item includes an article about a condition determined by the condition module 204.

In some examples, the group of content items form part of a content item pool. For example, the content item pool can include content items that have been submitted to a shared set of content items. In some examples, different creators create content to be uploaded to the content item pool. In some examples, the content item pool is accessible to clinician users through the content apparatus 104 via, for example, the data network 106. In such examples, the clinician users access the content item pool via a clinician user credential. In some examples, the content item pool is stored on a memory of an information handling device 102 (e.g., a computer in a clinician's office) and/or on a flash memory connected to the information handling device 102. In some examples, the content item pool is stored on the one or more servers 108.

In some examples, each content creator is a content creation user of the apparatus 104 who creates content to be uploaded to the content pool and accesses/uploads to the pool via, for example, a content creator credential. In some examples, the content item pool includes content items that are each created by content creators belonging to the same organization (e.g., a medical group, group of practitioners with admitting privileges at a common institution, a medical school, etc.). In other examples, the content item pool includes content items created by creators from different organizations but uploaded by users of the apparatus 104 from the same organization. In some examples, each of the content items is approved by an approval user of the apparatus 104 after creation but prior to being uploaded to the content item pool. In some examples, each approval user of the apparatus 104 belongs to the same organization.

In some examples, the content module 206 is configured to select a content item based at least in part on the condition determined by the condition module 204. In some examples, at least some of the content items in the content pool include tags indicating a condition. A tag includes, in some examples: a meta tag, a meta description tag, an HTML tag, a digital content tag, and/or any combination thereof. In some examples, an application includes a search function, and the tag is configured to include the digital content item in search results in response to keywords from the tag being searched. For example, a video about lung cancer includes a "lung cancer" tag. In some examples, the content items also include more general tags. For example, the lung cancer video also includes the tags "cancer" and "lung disease." In some examples, the content module 206 selects a content item having tags relating to the condition determined by the condition module 204. For example, the condition module 204 can determine that a clinician has diagnosed a patient with lung cancer. The content module 206 searches "lung cancer" in the content item pool and finds a video with a "lung cancer" tag. The content module 206 selects the video.

In some examples, the content module 206 is configured to select the content item by searching and/or filtering content in the content item pool. For example, the content module 206 can filter content by condition type. In some examples, the condition type is specific (e.g., "lung cancer" or "depression"). In other examples, the condition type is more general (e.g., "cancer", "lung disease", or "mental illness"). Additionally or alternatively, the content module 206 filters content by file type. For example, the content module 206 is configured to select one of each of a video, article, and infographic. In such examples, the content module 206 filters the content item pool by file type and selects content items accordingly.

In some examples, the content module 206 is configured to perform a keyword search. The content module 206 is configured to search the content item pool for the keywords and select content item(s) based on the search results. In some examples, the content module 206 generates a list of keywords including and/or relating to the condition. For example, the condition module 204 determines a health condition of "hip bursitis." The content module 206 generates a list of keywords that includes: "hip bursitis", "bursitis", "bursa inflammation", "hip pain", "hip inflammation", etc. In some examples, the content module 206 generates the keywords based at least in part on learned inferences of past conditions and keywords of content items selected for those conditions. In other examples, the list of keywords for a certain condition is pre-determined. In some examples, searching for the keywords includes searching at least one of the following for the items in the content pool: title, description, text, tags, and/or any combination thereof.

In some examples, the content module 206 is configured to select the content item based at least in part on learned inferences. For example, the content module 206 can make inferences based on past conditions and content items selected in connection with past conditions. In some examples, the learned inferences are based at least in part on a particular clinician user. For example, a clinician user diagnoses a patient with asthma. The content module 206 determines that the clinician user has frequently selected and/or approved a particular content item (e.g., an article) for previous patients diagnosed with asthma. In response to this determination, the content module 206 selects the content item. In some examples the content module 206 includes a machine learning model. The machine learning model is trained on historic associations between conditions determined by the condition module 204 and content approved by the clinician via the clinician approval module 208. In some examples, the machine learning model is configured to predict a content item to be selected based at least in part on the condition determined by the condition module 204. In some examples, the content module 206 selects a content item based at least in part on input from the machine learning model.

Figure 6:
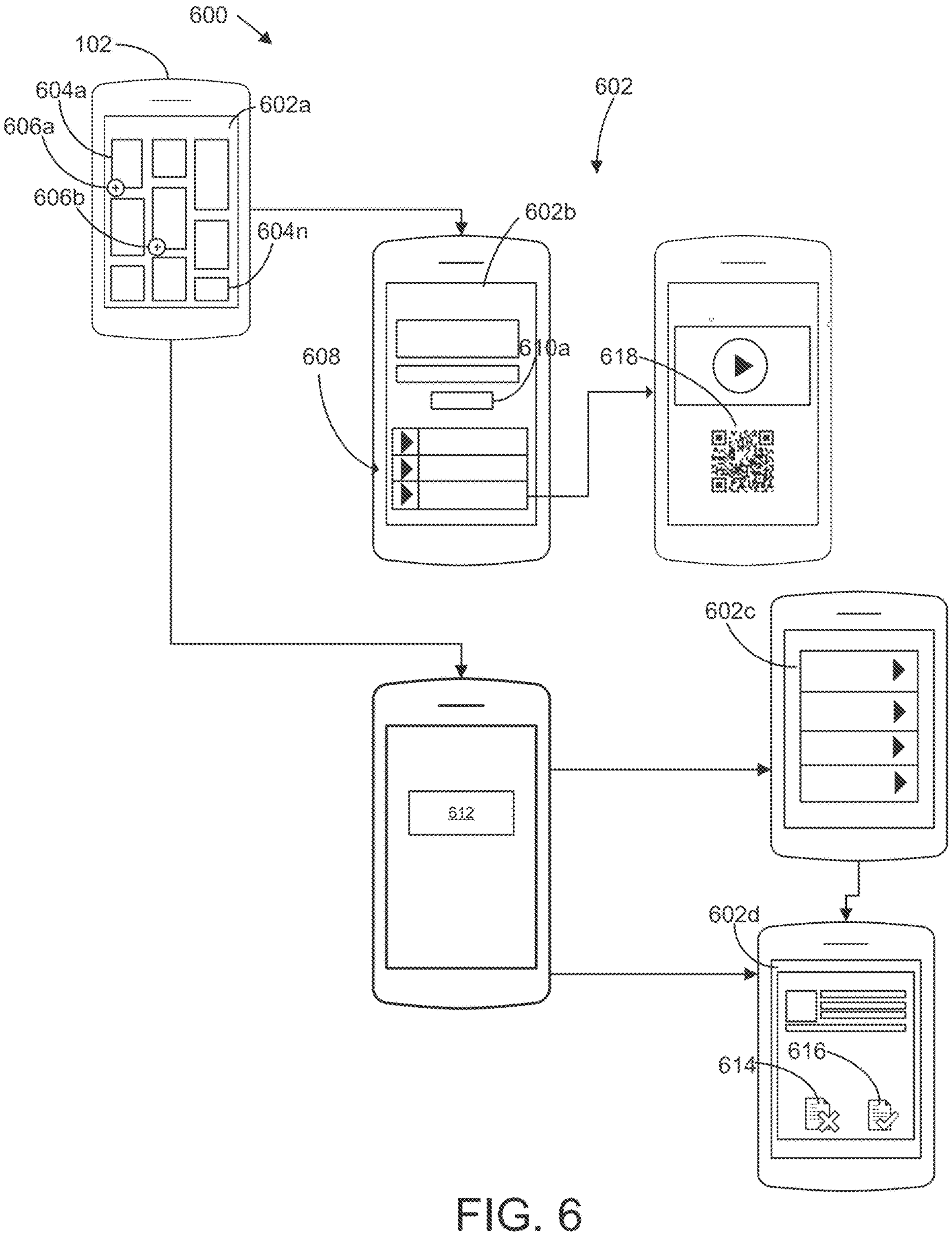
FIG. 6 is a schematic diagram illustrating one example of a GUI for creation, curation, approval, and delivery of health-related, educational content.

In some examples, the content module 206 is configured to select the content item based at least in part on direct clinician input. For example, as shown in FIG. 6, the content module 206 can present a clinician user interface 602 to the clinician user via, for example, a display of an information handling device 102. The user interface 602 includes representations 604*a*, 604*n* (referred to herein, individually and/or collectively, as "604") of various content items in the content item pool and buttons 606*a*, 606*b* (referred to herein, individually and/or collectively, as "606") selectable by the clinician user to select the content item(s). In some examples, the clinician user interface 602 is configured to allow the clinician user to search and/or filter the content item poo.

In some examples, the content module 206 is configured to select the content item based indirectly on clinician user input. In some examples, the clinician user inputs (e.g., via clinician user interface 602), a characteristic of the content item. For example, the clinician user can input a restriction of content items uploaded no earlier than three years prior. In some examples, the content module 206 narrows the content item pool and/or selects content based at least in part on that input.

The content module 206 is configured, in some examples, to select the content item based at least in part on a demographic of the patient. In some examples, the content module 206 is configured to determine a demographic of the patient based at least in part on at least one of the following: input from one or more sensors, input from the clinician user, input from a patient user, a patient user profile, and/or any combination thereof. Demographics include, for example: age, gender, race, native language, income, education level, and/or any combination thereof. In some examples, content items of the content item pool include tags relating to demographics. Tags include, for example, "Spanish" or "kid-friendly." For example, the content module 206 determines that the patient is a native Spanish speaker. In various examples, he content module 206 then selects content including Spanish text and/or audio. In another example, the content module 206 determines that the patient is a child. The content module 206 selects content that is more likely to be designed for and/or easily understood by children. For example, the content module 206 selects a video with a "kid-friendly" tag and/or content that depicts children in image and/or video form.

In some examples, the content module 206 is configured to generate a content item. For example, the content module 206 can include a generative artificial intelligence ("AI") model that is configured to generate a content item relating to a condition determined by the condition module 204. In some examples, the generative AI model is configured to generate, an article about the condition. In some examples, the generative AI model is trained on a corpus of content and conditions related to such content. In some examples, the corpus includes a corpus of content approved by a clinician for a user with a specific condition.

In some examples, the content module 206 is configured to select the content item in real time. For example, the content module 206 is configured to select the content item during a conversation and/or appointment between a patient and clinician. In such examples, the condition module 204 is configured to determine the condition in real-time. In another example, the content module 206 is configured to select the content item within a few minutes (e.g., five minutes) of the conclusion of an appointment. In some examples, the content module 206 is configured to select content items prior to an appointment between a clinician and a patient. For example, the condition module 204 can determine a condition based on input from the clinician, and the content module 206 selects one or more content items based on that condition without monitoring a conversation between a patient and a clinician.

In some examples, the content module 206 is configured to select a plurality of content items. In some examples, the selected content items include items of different types (e.g., a video file and an article).

In some examples, the clinician approval module 208 is configured to facilitate approval of a content item or content items. For example, the user interface 602*b* presents a list 608 of content items selected (e.g., selected by the clinician user via the interface 602*a*). In some examples, via the user interface 602*b*, the clinician user may add additional content items to the list 608 and/or delete content item(s) from the list 608. In some examples, the interface 602*a* also allows the clinician user to perform at least one of the following functions: input a message to the patient, re-ordering content items, saving the list 608 as a playlist of content items, and/or any combination thereof.

In some examples, the user interface 602*b* includes a button 610 selectable by the clinician user to approve the selected content item(s) by sending the selected content item to the patient user, along with any additions, deletions, edits and/or reordering performed by the clinician user. In other examples, the clinician approval module 208 is configured to receive the clinician approval via at least one of the following: e-mail message, text message, speech verification (e.g., via a microphone of an information handling device), and/or any combination thereof.

As shown in FIG. 6, in some examples, after the content module 206 selects the content, the clinician approval module 208 transmits a notification 612 to the clinician user to approve the content. In some examples, the notification 612 is configured to navigate the clinician user to a playlist detail page 602*c*. From the playlist detail page 602*c*, the clinician user may select individual content items to navigate to an approval page 602*d* for that particular content item. In some examples, the notification 612 navigates the device of the clinician user directly to the approval page 602*d* of a content item. In some examples, the approval page 602*d* includes at least one of the following: details regarding the content item, the content item embedded in the approval page 602*d*, an option 614 selectable to deny the content item, an option 616 selectable to approve the content item, and/or any combination thereof.

The webpage module 210 is configured to generate a webpage that includes the selected content item(s), based at least in part on the clinician approval module 208 receiving approval from the clinician. In some examples, the webpage module 210 is configured to generate a webpage in response to receiving approval from the clinician user. In other examples, the webpage module 210 is configured to generate a webpage before receiving approval from the clinician user, and the URL module 212 is configured to transmit the URL in response to receiving approval from the clinician user. For example, the webpage module 210 is configured to generate a webpage as shown on webpages 402*a*, . . . , 402*n* (referred to herein, individually or collectively, as "402") of FIG. 4. In some examples, the webpage module 210 is configured to generate the webpage without clinician approval. In some examples, the content module 206 is configured to automatically select content for the patient based at least in part on the condition (e.g., through AI analysis of the patient record). In some examples, in response, the webpage module 210 generates a webpage that includes the selected content.

Figure 4:
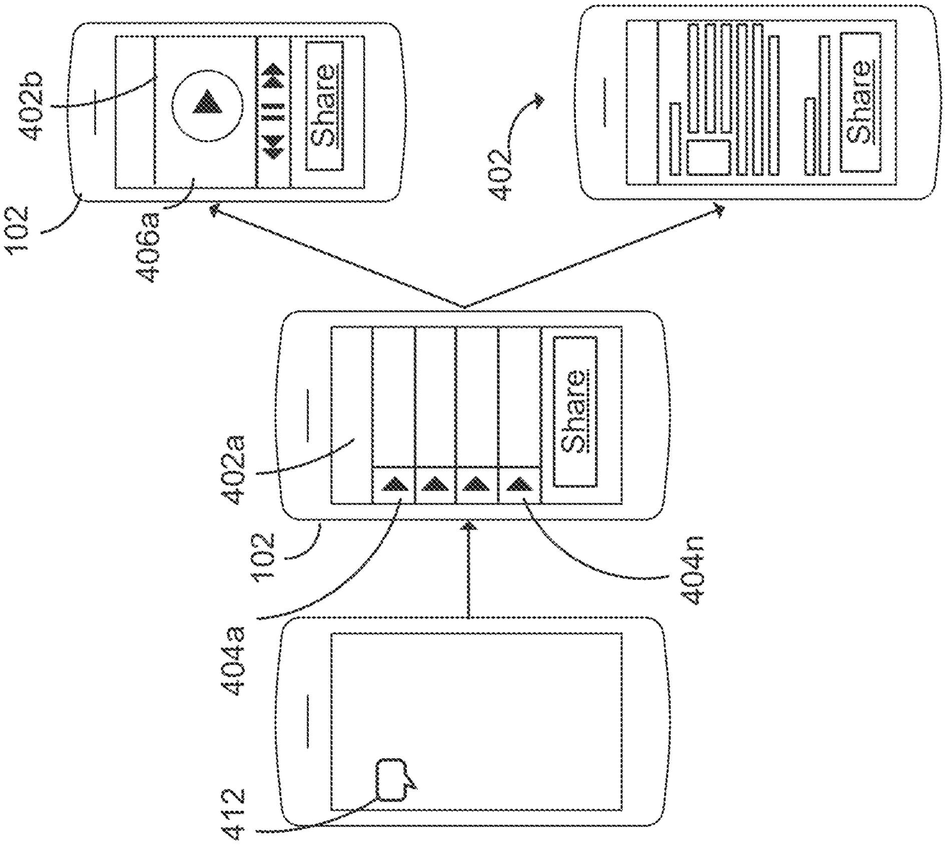
FIG. 4 is a schematic diagram illustrating one example of a graphical user interface ("GUI") for receiving and sharing health-related, educational content.

FIG. 4 illustrates a webpage 402*a*, which shows thumbnails 404*a*, . . . , 404*n* (referred to herein, individually or collectively, as "404"). In some examples, each thumbnail 404 represents a content item. In some examples, each thumbnail 404 is selectable to navigate to expand the thumbnail 404 and/or to navigate to another webpage (e.g., webpages 402*b*, . . . , 402*d*) to view the content item (e.g., content items 406*a*, . . . , 406*c*). For example, a content item 406*a* includes an embedded video. In another example, a content item 406*c* includes an article.

In some examples, the webpage 402 is a webpage of a user interface of an application. For example, the application is a web application and/or a mobile application. For example, the application is an electronic health records application. The patient user logs in to the application using a patient user credential. After logging in, the patient user can access, via the application, not only the webpage 402, but also their electronic health records.

The URL module 212 is configured to transmit a uniform resource locator ("URL") of the webpage generated by the webpage module 210 to a patient user. In some examples, the URL module 212 is further configured to transmit the URL to one or more additional users. For example, the URL module 212 references a patient user profile, which includes contact information for friends and/or family members. The URL module 212 transmits the URL to those friends/family members.

In some examples, the URL module 212 is configured to transmit the URL via at least one of the following: an e-mail message, a text message, a wireless connection, a notification within an application, or any combination thereof. For example, as shown in FIG. 4, the URL module 212, in some examples, is configured to transmit a notification 412 to the patient user and/or to additional users listed in a record of the patient user. As shown in FIG. 6, in some examples, the webpage module 210 is configured to generate a QR Code 618 that links to the URL. In some examples, the webpage module 210 is configured to export the QR Code 618 in a manner that can be printed from an information handling device 102 (e.g., into a PDF).

Figure 3:
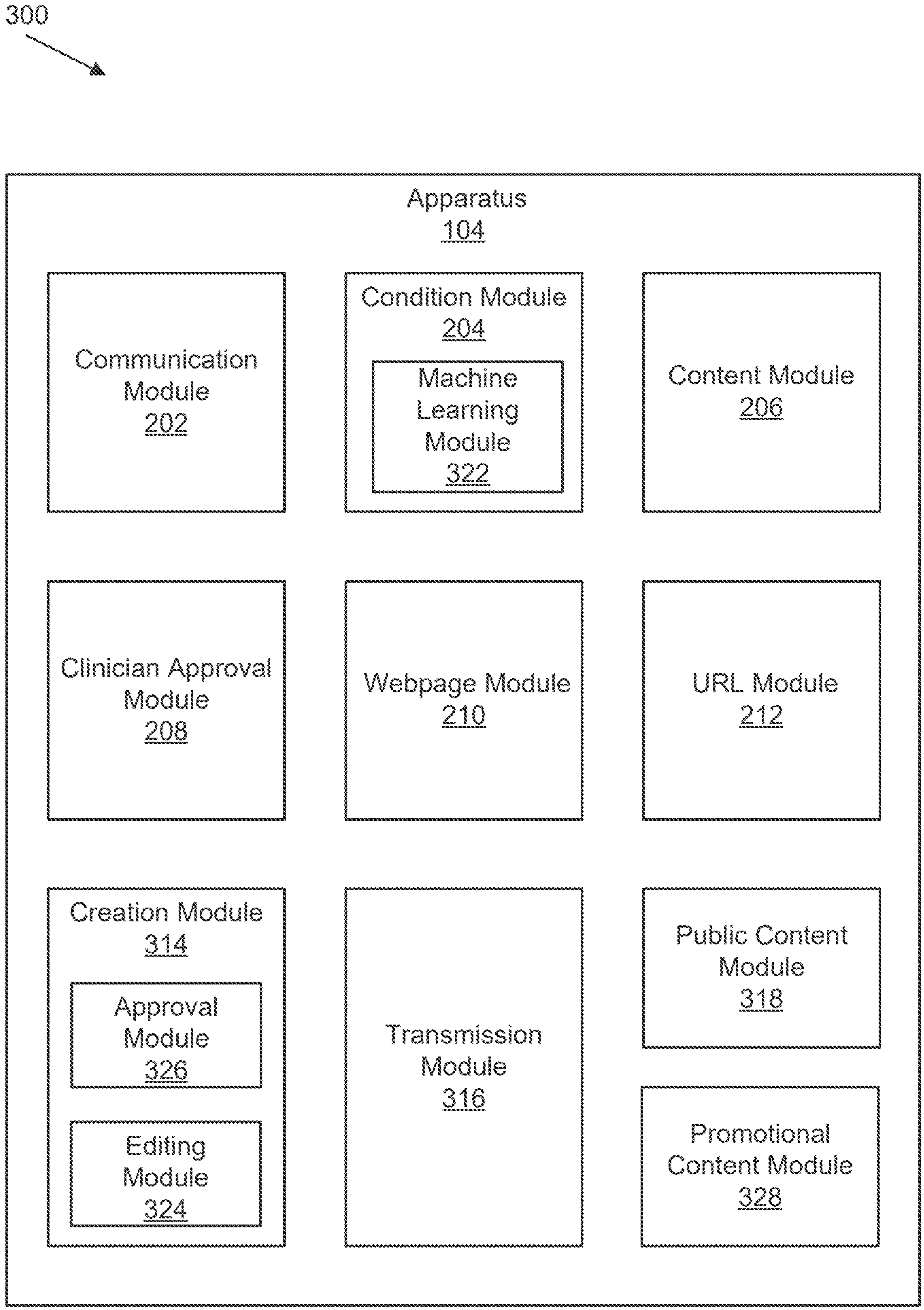
FIG. 3 is a schematic block diagram illustrating another example of an apparatus for electronic creation, curation, approval, and delivery of health-related, educational content.

FIG. 3 is a schematic block diagram illustrating one example of an apparatus 300 for electronic approval and delivery of health-related, educational content. In some examples, the apparatus 300 includes an example of the apparatus 200 and of a content apparatus 104. The content apparatus 104, in some examples, includes one or more of a condition module 204, a content module 206, a clinician approval module 208, a webpage module 210, and a URL module 212, as described in connection with FIG. 2. In some examples, the content apparatus 104 additionally includes a communication module 202, a creation module 314, a transmission module 316, a public content module 318, a machine learning module 322, an editing module 324, an approval module 326, and/or a promotional content module 328, as described in further detail below.

The communication module 202, in some examples, is configured to monitor, analyze, and/or listen to communication between a clinician user and a patient user. The communication being monitored includes, for example, oral conversation, non-verbal communication (e.g., gestures, facial expressions, etc.), written communication, and/or any combination thereof. In some examples, the communication being monitored includes a one-way communication from the clinician to the patient. In some examples, the communication includes two-way interaction between the clinician and the patient. In some examples, the communication takes place in person at, for example, a location of the clinician's practice (e.g., a hospital, office, clinic, etc.). In other examples, the communication occurs remotely. The communication can include a telephone conversation, virtual appointment, video call, and/or any combination thereof. In some examples, the communication includes a message transmitted from the clinician to the patient electronically. For example, the communication can include lab results sent electronically to the patient from the clinician.

In some examples, the communication module 202 is configured to record an interaction between a clinician and a patient, such as an exchange of digital messages and/or an oral conversation between a clinician and a patient. In some examples, the communication module 202 is configured to actively listen for a conversation and commence recording upon detecting a conversation between a doctor and a patient. For example, the communication module 202 records a conversation via an information handling device 102.

In some examples, the communication module 202 determines whether the communication includes a word and/or a phrase associated with a condition. For example, the condition module 204 references a database of words and phrases with associated conditions. In some examples, the condition module 204 is configured to convert a speech recording to text and analyze the text to determine the condition. In other examples, the condition module 204 is configured to determine the condition based on the raw audio of the speech.

In some examples, the condition module 204 is further configured to analyze content items within a content item pool and determine conditions associated with each content item. The condition module 204 is configured to determine a health condition related to the content item based at least in part on at least one of: input from a user, machine learning analysis of the content item, and/or any combination thereof. For example, the condition module 204 includes a machine learning module 322. In some examples, the machine learning module 322 is trained on a corpus of keywords, audio files, video files, images, transcribed text, content items, and/or any combination thereof. For example, an audio file includes a recording of a previous conversation between a patient and a clinician. In some examples, the training corpus also includes health conditions associated with each of those. For example, the corpus includes health data associated with the recording of the previous conversation, and the health data includes an indication of a discussed condition, such as "diabetes."

In some examples, the condition module 204 is further configured to tag a content item based at least in part on a health condition related to the content item. For example, the condition module 204 determines that a content item is related to heart disease. The condition module 204 then creates a search tag of "heart disease" for that content item.

In some examples, the creation module 314 is configured to receive content items to be added to the content pool. In some examples, the creation module 314 is also configured to provide a user interface for creating, editing, and/or submitting content items. In some examples, the user interface is provided on a mobile and/or web application that also presents user interface(s) other functions described herein, such as clinician approval, content publishing, and/or content transmission. In some examples, the content apparatus 104 presents a user having content creation permissions with an interface for creating, editing, and/or submitting content. For example, FIG. 5 includes an illustration 500 of an interface 502, which can include separate interfaces 502*a*, 502*b*, 502*c*. The interface 502 can include, for example, an interface 502*a* for recording a video and/or audio file, an interface 502*b* for adding a link to an article, an interface 502*c* for uploading a document to the content pool and/or to a pool of content to be sent to an approval user, an interface for creating an infographic, an interface for creating an interactive graphic, an interface for uploading any other type of educational content, and/or any combination thereof. In some examples, the creation module 314 is configured to create content via a device in which the content apparatus 104 resides, such as an information handling device 102. For example, the information handling device 102 can be a mobile phone, and the creation module 314 can be configured to create content using a video camera of the information handling device 102.

Figure 5:
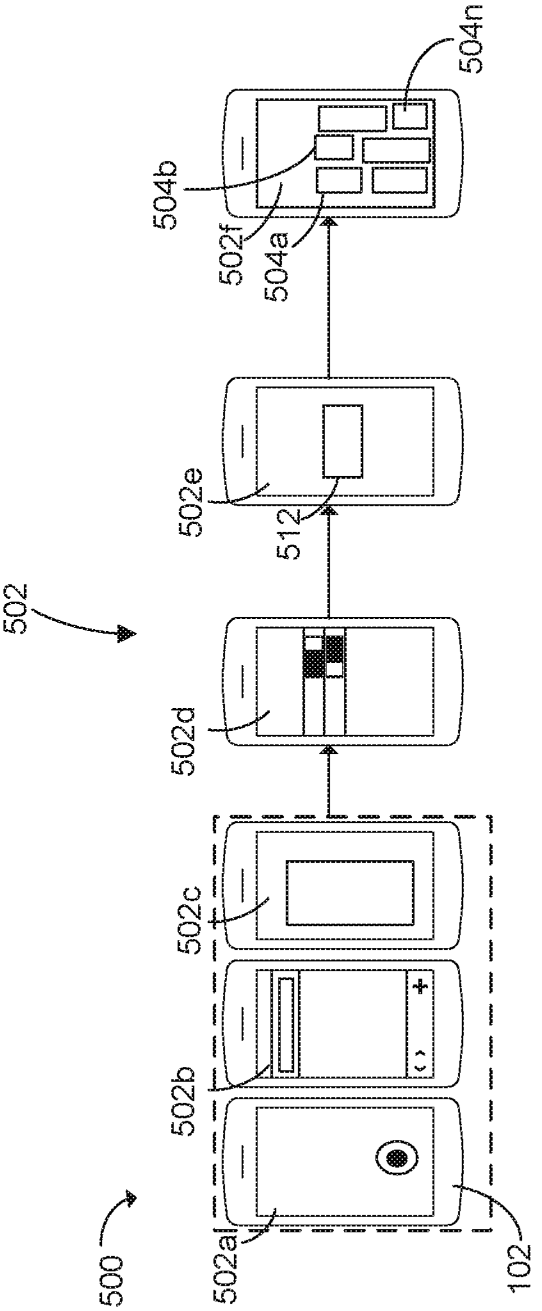
FIG. 5 is a schematic diagram illustrating one example of a GUI for approval of health-related, educational content.

In some examples, the creation module 314 is configured to implement settings, edits, and/or additions to the content based on user input. For example, the creation module 314 is configured to perform at least one of the following functions: adjust the speed of a video or audio, clip a video or audio, generate a summary of the content (using, for example, AI), set the content as "public" for publishing to a public forum, generating a transcript of a video or audio clip, inserting subtitles, setting content expiration dates, and/or any combination thereof. For example, as shown in FIG. 5, the content apparatus 104 can present content settings and editing interface 502*d* to the user.

In some examples, the creation module 314 is configured to display an approval workflow to a user before the user submits the content for approval (e.g., via an interface 502*e*). In some examples, the creation module 314 includes an approval module 326 configured to transmit the received content to one or more users with content approval permissions. The approval module 326 is further configured to receive approval from an approval user and, in response, add the content item to a content pool. In some examples, the approval module 326 is configured to submit a content item for approval and transmit a notification 512 to the user who created and/or submitted the content, indicating that the content has been submitted for approval. For example, the approval module 326 can transmit a notification to an approval user, indicating that approval is needed. For example, the approval module 326 can transmit the notification via an application, text message, e-mail message, and/or any combination thereof. In some examples, the notification navigates the device of the approval user to the content item.

Although not shown, in some examples, the approval module 326 generates a user interface with options selectable for the approval user to perform any of the following actions: approve the content, reject the content, edit the content, download the content, transmit the content to an additional user for approval, and/or any combination thereof. In some examples, rejecting the content includes adding approval user comments and/or redlined edits to the content and transmitting the content back to the user who submitted it. In some examples, editing the content includes receiving text input from the approval user and embedding the text input into the content item. In some examples, the editing module 324 is configured to implement any edits to the content item.

In some examples, the approval module 326 generates a record of approvals and/or rejections for each content item. In some examples, the record is stored in a memory accessible by the content apparatus 104. In some examples, the record includes at least one of the following: approval date, creation date, expiration date, prior versions of the content, identification of the approval user(s), and/or any combination thereof.

In some examples, the approval module 326 receives approval from a user without receiving the user's login credentials. For example, the approval module 326 transmits an approval request to an e-mail address and/or phone number that is associated with an approval user. In some examples, the approval user approves and/or rejects the content via an option selectable through a text and/or e-mail message.

In some examples, after the approval module 326 has submitted the content for approval, the approval module 326 updates an interface 502*f* displaying the content items in the content item pool. In some examples, the content pool interface 502*f* includes thumbnails 504*a*, . . . , 504*n* of the content items. The interface 502*f* is accessible, for example, by clinician users selecting content to send to patients and is analogous to the interface 602*a* of FIG. 6. In some examples, the thumbnails 504*a* of content items, which are still pending approval, appear differently from the thumbnails 504*b*, . . . , 504*n* which have been approved. For example, the thumbnails 504*a* of content pending approval are greyed out and/or contain an additional icon indicating the approval status. The thumbnails 504*a* of content pending approval are not selectable by a clinician user and/or by the content module 206 for sending to patient users.

The approval module 326 is configured to receive approval from a user with approval permissions. In response to receiving approval, the approval module 326 updates the interface 502*f* to indicate that the content item has been approved. For example, the thumbnail 504*a* is updated in at least one of the following ways: removing a "pending approval" indication, restoring color to the thumbnail, adding an option to select the content, and/or any combination thereof.

The transmission module 316 is configured to transmit a link to a webpage to a patient user. In some examples, the link is contained in a text message and/or e-mail message. In some examples, the link includes a hyperlink. In some examples, the link is configured to navigate a device (e.g., information handling device 102) of the patient user to the webpage 402 without tracking an IP address of the device. In some examples, the webpage 402 is a private webpage, such as a private webpage of a user interface of an application via which the user accesses electronic health records.

In some examples, the transmission module 316 is configured to schedule sending of content to patient users. In some examples, the transmission module 316 is configured to send and/or delay the webpage module 210 uploading content items to the webpage and/or the URL module 212 transmitting a URL to a patient user. For example, the transmission module 316 can determine, for a first content item, a first time and/or date to share the content item with the patient. For example, the transmission module 316 can determine, based at least in part on input from the clinician user, to send the user a video regarding their health condition an hour after the conclusion of an appointment. In response, the webpage module 210 generates the webpage with the video an hour after the appointment and transmits a link to the user at that time. In some examples, the transmission module 316 determines, based on input from the clinician user, to delay uploading a second video for at least a week after the first video. In response, the transmission module 316 instructs the webpage module 210 to delay uploading the second video for a week. As such, the transmission module 316 may help to distribute content to a patient at a schedule prescribed by a clinician rather than overwhelming the patient user with all of the selected content at the same time.

In some examples, the transmission module 316 instructs the webpage module 210 to not upload the second video to the webpage. Rather, the transmission module 316 instructs the webpage module 210 to generate a new webpage for the second video and instructs the URL module 212 to transmit a URL for the second webpage to the user at the scheduled time.

In some examples, as shown by interfaces 402*e* and 402*f* of FIG. 4, the transmission module 316 is configured to provide an option selectable for a patient user to share the URL for content items with family members and/or friends. For example, as shown in FIG. 4, the interfaces 402*e* and 402*f* provide options for sharing content by accessing contacts stored in an information handling device 102 of the patient user.

In some examples, the promotional content module 328 is configured to store one or more content items, such as promotional content items. In some examples, promotional content items are submitted by a user with administrative permissions. "Promotional content" includes, for example, information not directly linked to the content items and designed for viewing by more than one patient user. Examples of promotional content include, but are not limited to, announcements regarding upcoming clinical trials, reminders regarding clinic hours, reminders regarding insurance payments, information about upcoming events, and/or any combination thereof.

In some examples, the promotional content module 328 is configured to select a group of patient users to whom promotional content is transmitted. The group of patient users is based on, for example, at least one of the following: conditions associated with the user (e.g., determined by the condition module 204), geographical location, clinicians associated with the patient user, demographics, insurance provider, healthcare provider, locations at which the patient typically receives care, and/or any combination thereof. For example, the promotional content module 328 can store an announcement regarding a birthing class event at a hospital and selects a group of users with the condition of "pregnancy."

The promotional content module 328 is configured to upload the promotional content to webpages of URLs transmitted to the users (e.g., by URL module 212). For example, the promotional content module 328 can upload the promotional content to a webpage as text appearing underneath an embedded video content item.

Examples of the present disclosure include providing a user interface to a non-patient, administrative clinical trials user. In some examples, the promotional content module 328 receives input from the administrative clinical trials user. In some examples, the promotional content module 328 is configured to receive input from the administrative clinical trials user regarding timing of promotional content and update webpages and/or transmit new notifications to patient users accordingly.

The public content module 318 is configured to, in response to approval received via the approval module 326, publish a content item to a public domain. In some examples, the public domain includes a public website. In some examples, the public content module 318 is configured to publish the content item to the public domain in response to input received from a content creation user, such as a setting input by the content creation user. In some examples, the public content module 318 is configured to receive approval from a public content approval user. In some examples, the public content approval user is different from the approval user(s) approving content that is added to the content item pool without being published and is different from the clinician user.

Figure 7:
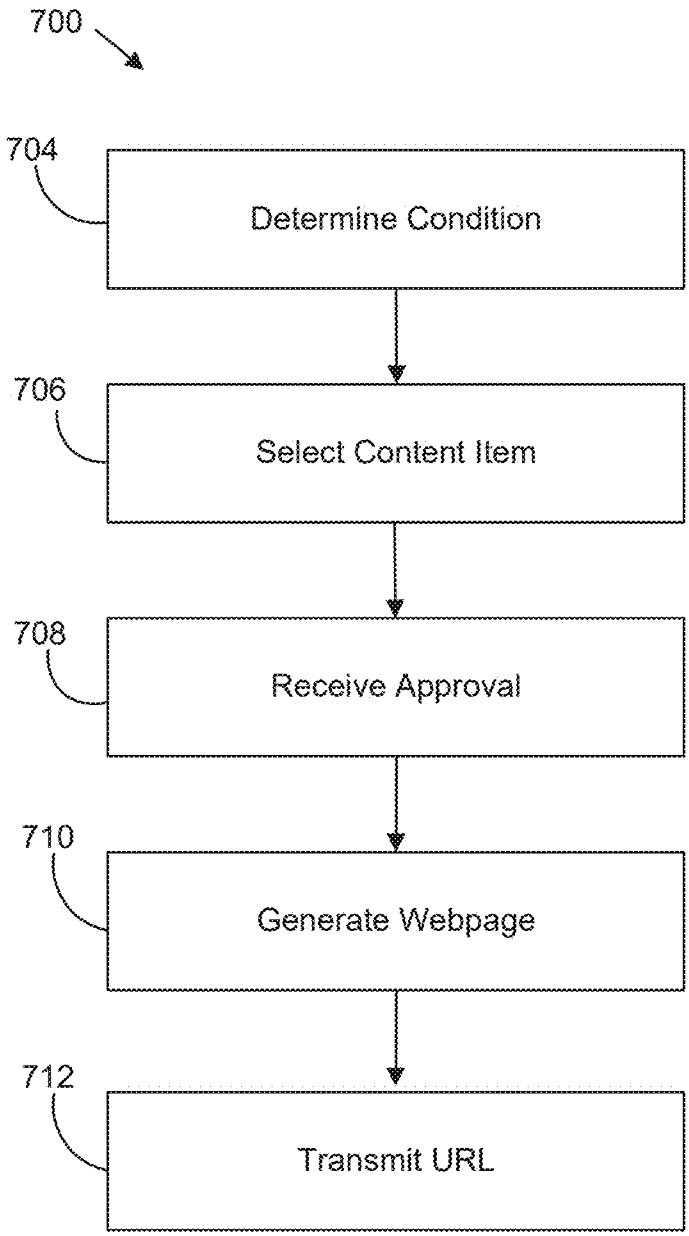
FIG. 7 is a flow chart illustrating one example of a method of creation, curation, approval, and delivery of health-related, educational content.

FIG. 7 is a schematic flow chart diagram illustrating one example of a method 700 of approval and delivery of health-related, educational content. In some examples, the method 700 begins and determines, in step 704, based at least in part on the communication, a condition associated with the patient user. The method 700 selects, at step 706, a content item from a group of content items. The method 700 receives, at step 708, approval of the content item from a clinician user. In some examples, the step 708 includes receiving approval from a device associated with a clinician user. The clinician user is associated with the patient user, in some examples. The method 700 generates, in step 710, a webpage comprising the content item. The method 700 transmits, at step 712, a uniform resource locator ("URL") of the webpage to the patient user. In some examples, some or all steps of the method 700 are implemented by module(s) of the apparatus 200 and/or 300.

Figure 8:
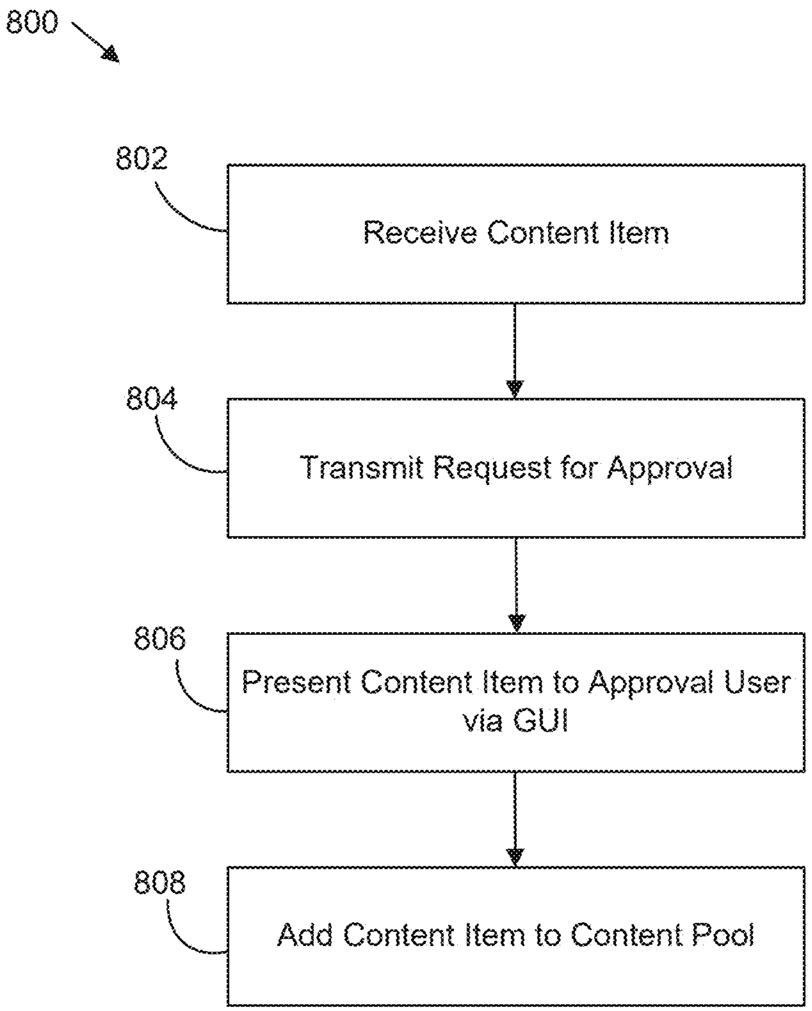
FIG. 8 is a flow chart illustrating another example of a method of approval of health-related, educational content.

FIG. 8 is a flow chart illustrating another example of a method 800 of approval and delivery of health-related, educational content. In some examples, the method 800 includes the steps of the method 700. In some examples, the method 800 receives, at step 802, a content item to be added to a content pool. In some examples, the method 800 receives the content item from a clinician user. The method 800 transmits 804, to an approval user, a request for approval of the content item. The method 800 presents, at step 806, to the approval user via a GUI, the content item and a button that is selectable to add the content item to the content pool. The method 800 adds, in step 808, in response to input from the approval user, the content item to the content pool. Adding the content item to the content pool includes, in some examples, displaying the content item to the clinician user and additional clinician users via an additional GUI.

Examples may be practiced in other specific forms. The described examples are to be considered in all respects only as illustrative and not restrictive. The scope of the subject matter disclosed herein is, therefore, indicated by the appended claims rather than by the foregoing description. All changes which come within the meaning and range of equivalency of the claims are to be embraced within their scope.

What is claimed is:

1. An apparatus, comprising:

a condition module that determines a condition associated with a patient user;

a content module that selects a content item from a group of content items based at least in part on the condition;

a clinician approval module that receives, from a clinician user associated with the patient user, approval of the content item prior to delivery of the content item to the patient user;

a webpage module that automatically generates, in response to and upon receipt of the approval, a private webpage comprising the content item; and a URL module that transmits a link to a uniform resource locator ("URL") of the private webpage to the patient user, wherein the link is configured to navigate a device of the patient user to the private webpage without tracking an Internet Protocol (IP) address of the device, wherein at least a portion of said modules comprise one or more of hardware circuits, programmable hardware circuits and executable code, the executable code stored on one or more computer readable storage media.

2. The apparatus of claim 1, wherein the URL module is further configured to transmit the URL via at least one of the following: an e-mail message, a text message, a wireless connection between the apparatus and a device associated with the patient user, or any combination thereof.

3. The apparatus of claim 1, wherein the content module is further configured to select the content item from the group of content items by selecting a plurality of content items from the group of content items based at least in part on the condition.

4. The apparatus of claim 1, wherein the webpage module is further configured to generate the private webpage by embedding the content item in the private webpage and the content item comprises at least one of the following: video content, audio content, an image, a graphic, an additional link, and/or any combination thereof.

5. The apparatus of claim 1, wherein the content item comprises educational material relating to the condition and the condition comprises at least one of: a characteristic of a patient's mental health, a characteristic of a patient's physical health, a diagnosis, or any combination thereof.

6. The apparatus of claim 1, wherein:

the private webpage comprises a private webpage of a user interface of an application;

electronic health records related to the patient user are accessible to the patient user via the application; and the application comprises at least one of a web application or a mobile application.

7. The apparatus of claim 1, wherein the content module is further configured to select the content item from the group of content items further based at least in part on at least one of: an association between the clinician user and the patient user, input from the clinician user, a patient demographic, or any combination thereof.

8. A method, comprising:

determining a condition associated with a patient user;

selecting a content item from a group of content items based at least in part on the condition;

receiving approval of the content item from a clinician user prior to delivery of the content item to the patient user, wherein the clinician user is associated with the patient user;

automatically generating, in response to and upon receipt of the approval, a private webpage comprising the content item; and transmitting a link to a uniform resource locator ("URL") of the private webpage to the patient user, wherein the link is configured to navigate a device of the patient user to the private webpage without tracking an Internet Protocol (IP) address of the device.

9. The method of claim 8, further comprising:

receiving a content item to be added to the group of content items;

transmitting, to an approval user, a request for approval of the content item;

presenting, to the approval user via graphical user interface (GUI):

the content item; and a button that is selectable to add the content item to the group of content items; and in response to input from the approval user selecting the button, adding the content item to the group of content items, wherein adding the content item to the group of content items comprises displaying the content item to the clinician user and additional clinician users via an additional GUI.

10. The method of claim 9, further comprising receiving text input from the approval user and embedding the text input into the content item.

11. The method of claim 9, further comprising selecting the content item from the group of content items subsequent to the content item being added to the group of content items.

12. The method of claim 11, wherein the clinician user is separate from the approval user.

13. The method of claim 8, wherein the condition comprises a health condition and the content item comprises at least one of video, audio, text, or image.

14. The method of claim 8, further comprising:

determining a health condition related to the content item based at least in part on at least one of input from a user or machine learning analysis of the content item; and tagging the content item based at least in part on the health condition related to the content item.

15. The method of claim 8, further comprising transmitting the link to the URL to one or more additional users associated with the patient.

16. The method of claim 8, wherein the content is downloadable from the private webpage.

17. The method of claim 8, further comprising:

storing one or more promotional content items;

selecting, based at least in part on the condition associated with the patient, a promotional content item of the promotional content items; and uploading the promotional content item to the private webpage.

18. The method of claim 8, further comprising:

determining a first time and/or first date to share the content item with the patient, wherein generating the private webpage and transmitting the link to the URL is performed at the determined first date and/or first time.

19. The method of claim 18, wherein:

the content item comprises a first content item; and the method further comprises:

determining, for a second content item, a second time and/or date to share the content item with the patient, wherein the second time and/or date is different from the first time and/or date; and on or after the second time and/or date, performing at least one of the following actions:

uploading the second content item to the private webpage; and generating an additional webpage displaying the second content item; and transmitting at least one of the link to the URL or an additional link to an additional URL of the additional webpage to the patient.

20. A program product comprising a non-transitory, computer readable storage medium that stores code executable by a processor, the executable code comprising code to perform:

determining a condition associated with a patient user;

selecting a content item from a group of content items based at least in part on the condition;

receiving approval of the content item from a clinician user prior to delivery of the content item to the patient user, wherein the clinician user is associated with the patient user;

automatically generating, in response to and upon receipt of the approval, a private webpage comprising the content item; and transmitting a link to a uniform resource locator ("URL") of the private webpage to the patient user, wherein the link is configured to navigate a device of the patient user to the private webpage without tracking an Internet Protocol (IP) address of the device.

* * * * *